(12) United States Patent
Palmer et al.

(10) Patent No.: US 7,818,154 B2
(45) Date of Patent: Oct. 19, 2010

(54) MONTE CARLO BASED MODEL OF FLUORESCENCE IN TURBID MEDIA AND METHODS AND SYSTEMS FOR USING SAME TO DETERMINE INTRINSIC FLUORESCENCE OF TURBID MEDIA

(75) Inventors: Gregory M. Palmer, Durham, NC (US); Nirmala Ramanujam, Chapel Hill, NC (US)

(73) Assignee: Duke University, Durham, NC (US)

( * ) Notice: Subject to any disclaimer, the term of this patent is extended or adjusted under 35 U.S.C. 154(b) by 334 days.

(21) Appl. No.: 11/725,141

(22) Filed: Mar. 16, 2007

(65) Prior Publication Data

US 2007/0232932 A1    Oct. 4, 2007

Related U.S. Application Data

(60) Provisional application No. 60/783,613, filed on Mar. 17, 2006.

(51) Int. Cl.
    G06F 1/00    (2006.01)
(52) U.S. Cl. .......................... 703/11; 707/102; 702/19; 356/244; 422/67; 436/172
(58) Field of Classification Search .................. 703/11; 707/102; 702/19; 356/244; 422/67, 82, 422/86; 436/172
    See application file for complete search history.

(56) References Cited

U.S. PATENT DOCUMENTS

| | | | |
|---|---|---|---|
| 4,580,895 A | 4/1986 | Patel | |
| 5,203,328 A | 4/1993 | Samuels et al. | |
| 5,439,578 A | 8/1995 | Dovichi et al. | |
| 5,452,723 A * | 9/1995 | Wu et al. | 600/342 |
| 5,529,391 A | 6/1996 | Kindman et al. | |
| 5,582,168 A | 12/1996 | Samuels et al. | |
| 5,813,403 A | 9/1998 | Soller et al. | |
| 5,924,981 A | 7/1999 | Rothfritz et al. | |
| 5,976,892 A | 11/1999 | Bisconte | |
| 6,055,451 A | 4/2000 | Bambot et al. | |
| 6,219,566 B1 | 4/2001 | Weersink et al. | |
| 6,411,373 B1 | 6/2002 | Garside et al. | |
| 6,564,088 B1 | 5/2003 | Soller et al. | |
| 6,577,391 B1 | 6/2003 | Faupel et al. | |
| 6,590,651 B1 | 7/2003 | Bambot et al. | |
| 6,678,541 B1 | 1/2004 | Durkin et al. | |
| 6,813,515 B2 | 11/2004 | Hashimshony | |
| 6,850,656 B1 | 2/2005 | Bevilacqua et al. | |
| 6,870,620 B2 | 3/2005 | Faupel et al. | |
| 6,912,412 B2 | 6/2005 | Georgakoudi et al. | |
| 6,965,345 B2 | 11/2005 | Bae et al. | |
| 6,975,899 B2 | 12/2005 | Faupel et al. | |
| 7,006,220 B2 | 2/2006 | Bambot et al. | |
| 7,030,988 B2 | 4/2006 | Kubo et al. | |
| 7,062,333 B2 | 6/2006 | Mizutani | |
| 7,064,837 B2 | 6/2006 | Mori et al. | |
| 7,082,325 B2 | 7/2006 | Hashimshony et al. | |
| 7,113,424 B2 | 9/2006 | Happ et al. | |
| 7,129,454 B2 | 10/2006 | O'Connell et al. | |
| 7,145,645 B2 | 12/2006 | Blumenfeld et al. | |
| 7,184,824 B2 | 2/2007 | Hashimshony | |
| 7,236,815 B2 | 6/2007 | Richards-Kortum et al. | |
| 7,411,680 B2 | 8/2008 | Chang et al. | |
| 7,570,988 B2 | 8/2009 | Ramanujam et al. | |
| 2002/0055671 A1 | 5/2002 | Wu et al. | |
| 2002/0114734 A1 | 8/2002 | Pantoliano et al. | |
| 2006/0247532 A1 | 11/2006 | Ramanujam et al. | |
| 2007/0019199 A1 | 1/2007 | Palmer et al. | |
| 2008/0056957 A1 | 3/2008 | Hayman | |
| 2008/0270091 A1 | 10/2008 | Ramanujam et al. | |

(Continued)

FOREIGN PATENT DOCUMENTS

WO    WO 02/40971 A1    5/2002

(Continued)

OTHER PUBLICATIONS

Palmer et al., "Monte Carlo-Based Inverse odel for Calculating Tissue Optical Properties. Part I: Theory and Valdiation on Synthetic Phantoms," Applied Optics, vol. 45, No. 5, pp. 1062-1071 (Feb. 10, 2006).

(Continued)

*Primary Examiner*—Mary K Zeman
(74) *Attorney, Agent, or Firm*—Jenkins, Wilson, Taylor & Hunt, P.A.

(57) ABSTRACT

The subject matter described herein includes a method for modeling fluorescence in turbid media and methods and systems for using the model to determine intrinsic fluorescence of turbid media. According to one aspect, a method for modeling fluorescence of a turbid medium and for using the model to determine intrinsic fluorescence in the turbid medium is provided. The method includes illuminating a turbid medium of interest with an electromagnetic radiation source using a probe of a particular geometry and detecting measured fluorescence for the turbid medium using the probe. At least one set of Monte Carlo simulations is run to determine an escape energy probability map and an absorbed energy density map for the turbid medium. An indication of the intrinsic fluorescence of the turbid medium is determined using the escape probability density map and the absorbed energy density map in a manner that accounts for the geometry of the probe.

20 Claims, 4 Drawing Sheets

U.S. PATENT DOCUMENTS

2009/0015826 A1    1/2009   Ramanujam et al.

FOREIGN PATENT DOCUMENTS

| WO | WO 2007/014188 A2 | 2/2007 |
|---|---|---|
| WO | WO 2007/109126 A2 | 9/2007 |
| WO | WO 2008/103486 A1 | 8/2008 |
| WO | WO 2009/043045 A1 | 4/2009 |
| WO | WO 2009/043050 A2 | 4/2009 |
| WO | WO 2009/132360 A2 | 10/2009 |

OTHER PUBLICATIONS

Palmer et al., "Monte Carlo-Based Inverse Model for Calculating Tissue Optical Properties. Part II: Application to Breast Cancer Diagnosis," Applied Optices, vol. 45, No. 5, pp. 1072-1078 (Feb. 10, 2006).

Chang et al., "Analytical Model to Describe Fluorescence Spectra of Normal and Preneoplastic Epithelial Tissue: Comparison with Monte Carlo Simulations and Clinical Measurements," Journal of Biomedical Optics, vol. 9, No. 3, pp. 511-522 (May/Jun. 2004).

Biswal et al., "Recovery of Turbidity Free Fluorescence from Measured Fluorescence: An Experimental Approach," Optics Express, vol. 11, No. 24, pp. 3320-3331 (Dec. 1, 2003).

Diamond et al., "Quantification of Fluorophore Concentration in Tissue-Simulating Media by Fluorescence Measurements with a Single Optical Fiber," Applied Optics, vol. 42, No. 13, pp. 2436-244 (May 1, 2003).

Swartling et al., "Accelerated Monte Carlo Models to Simulate Fluorescence Spectra from Layered Tissues," Journal of Optical Society of America, vol. 20, No. 4, pp. 714-727 (Apr. 2003).

Diamond et al., "Measurement of Fluorophore Concentrations and Fluorescence Quantum Yield in Tissue-Simulating Phantoms Using Three Diffusion Models of Steady-State Spatially Resolved Fluorescence," Physics in Medicine and Biology, vol. 48, pp. 4135-4149 (2003).

Ma et al., "Determination of Complex Refractive Index of Polystyrene Microspheres from 370 to 1610 nm," Physics in Medicine and Biology, vol. 48, pp. 4165-4172 (2003).

Weersink et al., "Noninvasive Measurement of Fluorophore Concentration in Turbid Media with a Simple Fluorescence/Reflectance Ratio Technique," Applied Optics, vol. 40, No. 34, pp. 6389-6395 (Dec. 1, 2001).

Müller et al., "Intrinsic Fluorescence Spectroscopy in Turbid Media: Disentangling Effects of Scattering and Absorption," Applied Optics, vol. 40, No. 25, pp. 4633-4646 (Sep. 1, 2001).

Ramanujam, "Fluorescence Spectroscopy in Vivo," Encyclopedia of Analytical Chemistry, pp. 20-56 (2000).

Yu et al., "Quasi-Discrete Hankel Transform," Optical Letters, vol. 23, No. 6, pp. 409-411 (Mar. 15, 1998).

Chance et al., "Biochemical Distinctions Between Normal and Cancerous Human Breast Tissues Obtained from Fluorescence Spectroscopy," Proceedings of Optical Tomography and Spectroscopy of Tissue: Theory, Instrumentation, Model, and Human Studies II, Biomedical Optics, vol. 2979, pp. 585-588 (Feb. 9-12, 1997).

Zhang et al., "Innate Cellular Fluorescence Reflects Alterations in Cellular Proliferation," Lasers in Surgery and Medicine, vol. 20, pp. 319-331 (1997).

Gardner et al., "Fluorescence Spectroscopy of Tissue: Recovery of Intrinsic Fluorescence from Measured Fluorescence," Applied Optics, vol. 35, No. 10, pp. 1780-1792 (Apr. 1, 1996).

Graaff et al., "Condensed Monte Carlo Simulations for the Description of Light Transport," Applied Optics, vol. 32, No. 4, pp. 426-434 (Feb. 1, 1993).

Zhu et al., "Diagnosis of Breast Cancer Using Diffuse Reflectance Spectroscopy: Comparison of a Monte Carlo Versus Partial Least Squares Analysis Based Feature Extraction Technique," Lasers in Surgery and Medicine, vol. 38, pp. 714-724 (2006).

Palmer, "Experimental, Computational, and Analytical Techniques for Diagnosing Breast Cancer Using Optical Spectroscopy," Dissertation, University of Wisconsin-Madison, pp. 1-188 (2005).

Amelink et al., "Measurement of the Local Optical Properties of Turbid Media by Differential Path-Length Spectroscopy," Applied Optics, vol. 43, No. 15, pp. 3048-3054 (May 20, 2004).

Breslin et al., "Autofluorescence and Diffuse Reflectance Properties of Malignant and Benign Breast Tissues," Annals of Surgical Oncology, vol. 11, No. 1, pp. 65-70 (Mar. 31, 2004).

Mourant et al., "Measuring Absorption Coefficients in Small Volumes of Highly Scattering Media: Source-Detector Separations for which Path Lengths do not Depend on Scattering Properties," Applied Optics, vol. 36, No. 22, pp. 5655-5661.

Interview Summary for U.S. Appl. No. 11/493,020 (Nov. 17, 2009).

Liu et al., "Sequential Estimation of Optical Properties of a Two-layered Epithelial Tissue Model From Depth-Resolved Ultraviolet-visible Diffuse Relectance Spectra," Applied Optics, vol. 45, No. 19, pp. 4776-4790 (Jul. 1, 2006).

Official Action for U.S. Appl. No. 11/729,967 (May 28, 2009).

PCT International Application Serial No. PCT/US09/41857 for "Systems and Methods for Performing Optical Spectroscopy Using a Self-Calibrating Fiber Optic Probe" (Apr. 27, 2009).

Office Action for U.S. Appl. No. 11/493,020 (Apr. 24, 2009).

PCT International Application Serial No. PCT/US09/41732 for "A Diffuse Reflectance Spectroscopy Device for Quantifying Tissue Absorption and Scattering" (Apr. 24, 2009).

Restriction and/or Election Requirement for U.S. Appl. No. 11/729,967 (Apr. 17, 2009).

Notification of Transmittal of the International Search Report and the Written Opinion of the International Searching Authority, or the Declaration for International Application No. PCT/US2008/078194 (Apr. 17, 2009).

Notification of Transmittal of the International Search Report and the Written Opinion of the International Searching Authority, or the Declaration for International Application No. PCT/US2008/078186 (Feb. 17, 2009).

Restriction and/or Election Requirement for U.S. Appl. No. 11/493,020 (Feb. 10, 2009).

Communication of European Publication Number and Information on the Application of Article 67(3) EPC for European Patent No. 2001352 (Nov. 19, 2008).

Notification of Transmittal of the International Search Report and the Written Opinion of the International Searching Authority, or the Declaration for International Application No. PCT/US07/07586 (Oct. 7, 2008).

Notification of Transmittal of the International Search Report and the Written Opinion of the International Searching Authority, or the Declaration for International Application No. PCT/US08/02431 (Jun. 19, 2008).

Notification of Transmittal of the International Search Report and the Written Opinion of the International Searching Authority, or the Declaration for International Application No. PCT/US06/28770 (Mar. 12, 2008).

Communication of European Publication Number and Information on the Application of Article 67(3) EPC for European Application No. 06800300.3 (Mar. 12, 2008).

Liu et al., "Scaling Method for Fast Monte Carlo Simulation of Diffuse Reflectance Spectra from Multilayered Turbid Media," J. Opt. Soc. Am. A, vol. 24, No. 4, pp. 1011-1025 (Apr. 2007).

Notice of Allowance and Fee(s) Due for U.S. Appl. No. 11/729,967 (Oct. 22, 2009).

Interview Summary for U.S. Appl. No. 11/729,967 (Sep. 24, 2009).

Notification of Transmittal of the International Search Report and the Written Opinion of the International Searching Authority, or the Declaration for International Application No. PCT/US2009/041732 (Apr. 15, 2010).

Notice of Allowance and Fee(s) Due for U.S. Appl. No. 11/493,020 (Mar. 10, 2010).

Extended European Search Report for European Patent No. 2001352 (Mar. 5, 2010).

Notice of Allowance and Fee(s) Due for U.S. Appl. No. 11/729,967 (Feb. 19, 2010).

Notice of Allowance and Fee(s) Due for U.S. Appl. No. 11/119,865 (May 1, 2009).

Final Official Action for U.S. Appl. No. 11/119,865 (Mar. 18, 2009).

Communication of European Publication Number and Information on the Application of Article 67(3) EPC for European Patent No. 2005173 (Nov. 26, 2008).

Official Action for U.S. Appl. No. 11/119,865 (Jul. 11, 2008).

Georgakoudi et al., "NAD(P)H and Collagen as inVivo Quantitative Fluorescent Biomarkers of Epithelial Precancerous Changes," Cancer Research, vol. 62, p. 682-687 (Feb. 1, 2002).

Pogue et al., "Fiber-Optic Bundle Design for Quantitative Fluorescence Measurement From Tissue," Applied Optics, vol. 37, Issue 31, p. 7429-7436 (Nov. 1, 1998).

* cited by examiner

MONTE CARLO BASED MODEL OF FLUORESCENCE IN TURBID MEDIA AND METHODS AND SYSTEMS FOR USING SAME TO DETERMINE INTRINSIC FLUORESCENCE OF TURBID MEDIA

CROSS REFERENCE TO RELATED APPLICATIONS

This application claims the benefit of U.S. Provisional Patent Application Ser. No. 60/783,613, filed Mar. 17, 2006, the disclosure of which is incorporated herein by reference in its entirety.

GOVERNMENT INTEREST

This presently disclosed subject matter was made with U.S. Government support under Grant No. 1R01CA00599-01A1 and Grant No. 5T32CA009206-27 awarded by the National Institutes of Health. Thus, the U.S. Government has certain rights in the presently disclosed subject matter.

TECHNICAL FIELD

The subject matter described herein relates to analyzing fluorescence spectra of turbid media. More particularly, the subject matter described herein relates to a Monte Carlo based model of fluorescence spectra of turbid media and methods and systems for using the model to determine an indication of intrinsic fluorescence of turbid media.

BACKGROUND

Fluorescence spectroscopy has been used successfully for discriminating malignancy at a number of organ sites (Ramanujam, 2000 [1]). However, due to the complex interplay of absorption, scattering, and fluorescence interaction in turbid media, such as biological tissue, it can be difficult to separate the effects of fluorescence from absorption and scattering, thus making these spectra difficult to interpret.

To address this issue, a number of groups have proposed methods for determining the fluorophore concentration or intrinsic fluorescence spectra (i.e., the fluorescence properties independent of absorption and scattering) from a measured fluorescence spectrum (see e.g., Sinaasappel & Sterenborg, 1993; Wu et al., 1993; Durkin et al., 1994; Gardner et al., 1996; Zhadin & Alfano, 1998; Ramanujam, 2000; Zhang et al., 2000; Muller et al., 2001; Weersink et al., 2001; Biswal et al., 2003; Diamond et al., 2003; Swartling et al., 2003; Chang et al., 2006 [2]-[14]). These approaches include empirical calibration, diffusion theory modeling, and Monte Carlo modeling of fluorescence. However, these approaches have generally been limited in that they are valid for only a limited range of absorption and scattering, they require extensive empirical calibration, and/or they are not flexible in their applicability to a range of probe geometries.

What are needed, then, are robust methods for extracting intrinsic fluorescence from turbid media. To address this need, at least in part, the subject matter described herein includes a Monte Carlo based model of fluorescence of turbid media and methods and systems for using the model to determine intrinsic fluorescence of turbid media.

SUMMARY

The subject matter described herein includes a method for modeling fluorescence in turbid media and methods and systems for using the model to determine intrinsic fluorescence of turbid media. According to one aspect, a method for modeling fluorescence of a turbid medium and for using the model to determine intrinsic fluorescence in the turbid medium is provided. The method includes illuminating a turbid medium of interest with an electromagnetic radiation source using a probe of a particular geometry and detecting measured fluorescence for the turbid medium using the probe. At least one set of Monte Carlo simulations is run to determine an escape energy probability map and an absorbed energy density map for the turbid medium. An indication of the intrinsic fluorescence of the turbid medium is determined using the escape probability density map and the absorbed energy density map in a manner that accounts for the geometry of the probe.

As used herein, the term "turbid medium" includes a medium that has at least one of scatters and absorbers that reduce the amount of incident light that reaches fluorophores in the medium and/or that reduce the amount of photons emitted from fluorophores in the medium that escape the medium. One example of a turbid medium with which the subject matter described herein may be used is biological tissue, such as a human tissue sample As used herein, the phrase "intrinsic fluorescence" refers to a quantity of emitted by fluorophores in a turbid medium that is independent of the presence of scatters or absorbers in the turbid medium.

BRIEF DESCRIPTION OF THE DRAWINGS

Preferred embodiments of the subject matter described herein will now be explained with reference to the accompanying drawings, of which:

FIG. 3A is a plot of normalized extracted intrinsic fluorescence spectra. The fluorescence spectral line shape acquired with no absorber or scatterer present is also shown (black line) and can be seen to be very similar to the extracted line shape. FIG. 3B is a plot of non-normalized extracted intrinsic fluorescence spectra. For comparison, plot of the original fluorescence spectra are shown in FIGS. 3C and 3D. The original fluorescence spectra exhibited significant differences in intensity and line shape. In all plots, the phantom with the highest absorption and scattering properties is depicted using solid black circles.

DETAILED DESCRIPTION

Figure 1:
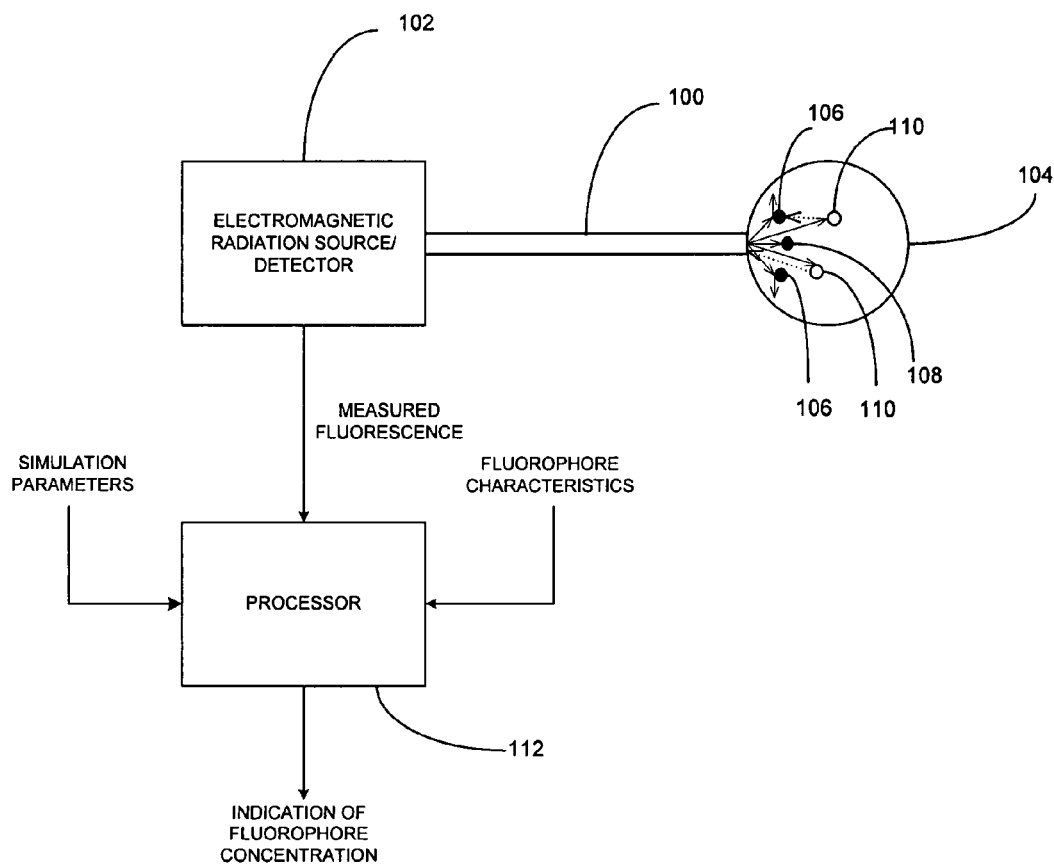
FIG. 1 is a block diagram of a system for obtaining fluorescence measurements in turbid media, for modeling fluorescence in turbid media, and for determining, using the model, an indication of intrinsic fluorescence of turbid media according to an embodiment of the subject matter described herein.

The subject matter disclosed herein includes a Monte Carlo based model of fluorescence in turbid medium and methods and systems for using the model to determine an indication of intrinsic fluorescence of the turbid medium. FIG. 1 illustrates an exemplary system in which the presently disclosed subject matter may be used. In FIG. 1, a probe 100 and an electromagnetic radiation source/detector 102 may be used to illuminate a turbid medium 104 and detect fluorescence generated by fluorophores present in turbid medium 104. However, due to the presence of scatterers 106 and absorbers 108, some of the incident photons, indicated by solid arrows in FIG. 1, will not contact fluorophores in turbid medium 104 because the incident photons will be scattered or absorbed. In addition, even when the incident photons contact fluorophores 110 and cause fluorophores 110 to emit fluorescent photons, the emitted fluorescent photons, indicated by the dotted arrows in FIG. 1, may likewise be scattered or absorbed by scatterers 106 or absorbers 108. Further, even for the emitted fluorescent photons that exit turbid medium 104, only a portion will be detected by probe 100 due to its detection surface geometry. In addition, the emission surface geometry of probe 100 results in less than complete coverage of turbid medium 104 with incident photons. As a result, scattering, absorption, and probe geometry must be accounted for in a model that determines intrinsic fluorescence of turbid medium 104.

In order to account for the effects of probe geometry, scatters, and absorbers on fluorescence measurements, the system illustrated in FIG. 1 includes a processor 112 that runs one or more simulations to generate a model of fluorescence in turbid media 104 and that uses the model to generate an indication of the intrinsic fluorescence of the turbid medium. Processor 112 may receive as input simulation start parameters, such as a set of arbitrarily selected optical properties of a turbid medium. In one implementation, these optical properties may include absorption coefficient, scattering coefficient, anisotropy factor, and refractive index. If the indication of intrinsic fluorescence to be determined is the concentration of one or more fluorophores, processor 112 may receive as input fluorophore characteristics, such as the extinction coefficient of the fluorophore at the excitation wavelength, the probability that a photon absorbed by a fluorophore will generate fluorescence, and the spectral probability distribution of the generated fluorescence at the emission wavelength. If these properties of the fluorophore are determined, then the concentration of the fluorophore in turbid medium 104 can be determined. If these properties and not provided as input to processor 112, the indicator of intrinsic fluorescence may be an alternate measure of intrinsic fluorescence, such as the product of the quantum yield and the fluorophore concentration.

Figure 2:
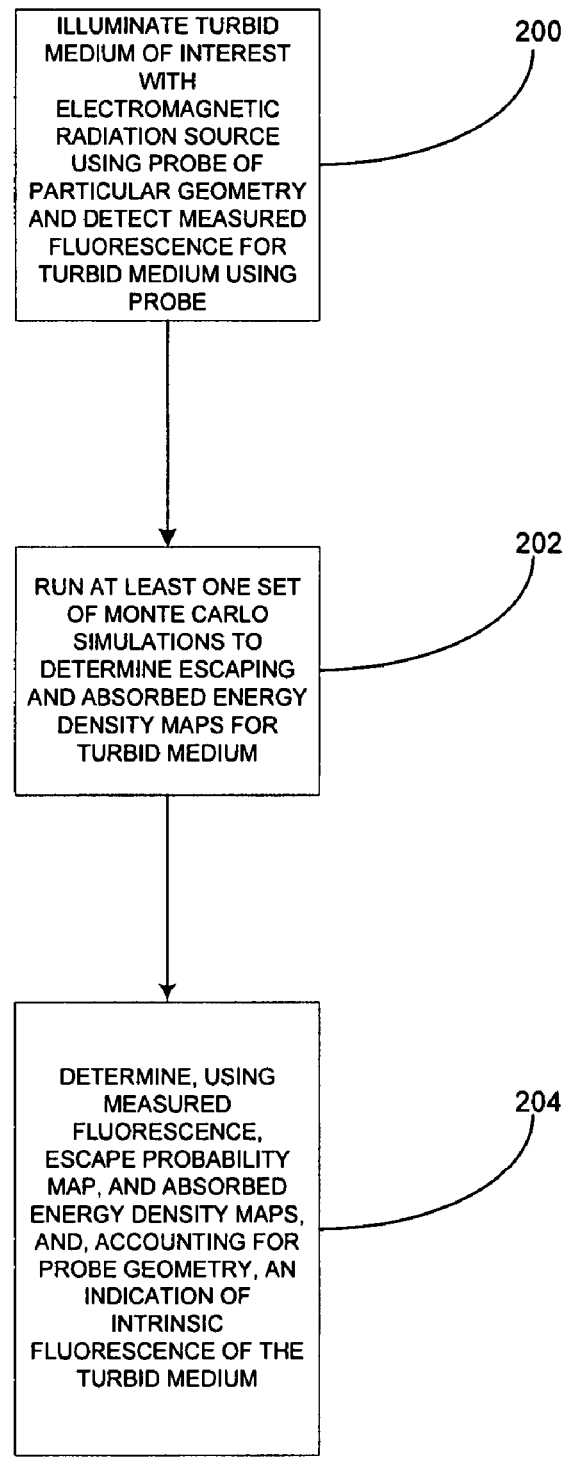
FIG. 2 is a flow chart illustrating an exemplary process for modeling fluorescence in turbid media and for using the model to determine an indication of intrinsic fluorescence of turbid medium according to an embodiment of the subject matter described herein.

FIG. 2 is a flow chart illustrating an exemplary process for modeling fluorescence of turbid media and for using the model to determine intrinsic fluorescence of the turbid medium according to an embodiment of the subject matter described herein. Referring to FIG. 2, in step 200, a turbid medium of interest is illuminated with an electromagnetic radiation source using a probe of a specified geometry and measured fluorescence is detected using the probe. In FIG. 1, probe 100 may be used to illuminate turbid medium 104 via electromagnetic radiation source 102, and fluorescent light emitted by turbid medium 104 due to the presence of fluorophores in turbid medium 104 may be detected. Probe 100 may be a fiber optic probe with one or more emission fibers and one or more collection fibers. In addition, some fibers may be both collection and emission fibers. An exemplary method for optimizing the design of probe 100 for measuring fluorescence in turbid media is found in U.S. patent application publication number 20070029299, published on Jan. 25, 2007, the disclosure of which is incorporated herein by reference in its entirety. Electromagnetic radiation source/detector 102 may include a broadband light source, a narrowband light source, or both.

Returning to FIG. 2, in block 202, at least one set of Monte Carlo simulations is run to determine escape energy probability map and absorbed energy density map for the turbid medium. In one exemplary implementation, two separate sets of Monte Carlo simulations may be run—one for photons originating from outside of a turbid medium to determine the absorbed energy density map and another for photons emitted from within the turbid medium to determine the escape energy probability map. In an alternate implementation, a single Monte Carlo simulation may be run for photons emitted from within the turbid medium to determine the escape energy probability map, and a reciprocity principle may be used to determine the absorbed energy density map. Details of the Monte Carlo simulations are described below.

In step 204, an indication of the intrinsic fluorescence of the turbid medium is determined, accounting for the probe geometry and using the measured fluorescence, the absorbed energy density map, and the escape energy probability map. In one implementation, as will be described below, the indication of intrinsic fluorescence is the product of the quantum yield and the concentration of one or more fluorophores. In an alternate implementation, the indication of the intrinsic fluorescence is the actual concentration of the fluorophore. The probe geometry is accounted for in the determination using a convolution operation that considers the surface areas of the collection and illumination fiber(s) of the probe and photons escaping the turbid medium emitted from a point source within the medium. Because the probe geometry is accounted for in the determination, the present subject matter may be used to determine the indication of the intrinsic fluorescence given fluorescence measured by any probe geometry. In addition, the indication of the intrinsic fluorescence is independent of absorption and scattering effects of the turbid medium.

In an analogy, the present subject matter converts fluorescence measurement made in a turbid medium, such as milk, to a measurement made in a translucent medium, such as water. Once the measurement has been converted to a value that would have been measured in a translucent medium, the fluorophore concentration can be determined given known properties of the fluorophore of interest, such as quantum yield. The Monte Carlo based model for effecting this conversion will now be described in detail.

In the present approach, the Monte Carlo based model of diffuse reflectance described in Palmer and Ramanujam, 2006 [15, 16] is first used to extract the optical properties of the turbid medium. As stated above, the optical properties may include scattering coefficient, absorption coefficient, anisotropy factor, and refractive index of the turbid medium. The optical properties are incorporated into the model of fluorescence to incorporate the intrinsic fluorescence from the turbid medium into the model.

Swartling et al., 2003 outline a technique wherein a single Monte Carlo simulation can generate the fluorescence spectrum for any set of optical properties [11]. Their approach is the break the Monte Carlo simulation into two separate simulations, one dealing with the excitation light traveling from the light source to the tissue fluorophore, and one dealing with the emitted fluorescence traveling from the fluorophore to the detector. In this way, each of the two component simulations can be scaled, using a variety of approaches, to any arbitrary set of optical properties. One exemplary implementation of the subject matter described herein follows their approach with a few notable differences. First, the scaling relations described by Graff et al., 1993 [17] were incorporated into the present model to enable the fluorescence model to be scaled to any arbitrary set of optical properties. These scaling relationships have the advantage of being able to accurately describe the effects of absorption outside of the diffusion regime.

Secondly, the quasi discrete Hankel transform described in Li et al., 1998 [18] was used to convolve the absorption and emission simulation data, enabling greater speed, which is important for clinical applications. Third, a convolution scheme (described in Palmer and Ramanujam, 2006 [15]) was used to model the probe geometry, enabling this model to be applied to any arbitrary probe geometry. Finally, a framework is developed by which these forward simulation techniques can be applied to perform the reverse problem of determining the intrinsic fluorescence properties from measured fluorescence spectra. This is done by incorporating a diffuse reflectance Monte Carlo model to calculate optical properties, which are then used to solve for the intrinsic fluorescence properties of the tissue, independent of absorption and scattering, as outlined below.

As described above, either a single set of Monte Carlo simulations or two sets of Monte Carlo simulations may be run to determine the absorbed and escape energy density maps. In the present example, a single set of Monte Carlo Simulations was run to determine an escape energy density map, and an absorbed energy density map using a reciprocity principle. In this example, Monte Carlo simulations were run to generate an escape fluorescence energy probability map $E(r_i, z_i)$. Photons were launched over a series of depth increments from within a turbid medium with an arbitrary set of optical properties. In this example, the depth increments used ranged from 0 to 1 cm, in 0.005 cm increments, with 100,000 photons being launched at each increment. A depth of 1 cm was chosen, since depths greater than this were found to have negligible contribution to the measured fluorescence. The following parameters were used: absorption coefficient $\mu_a=0.01$ cm$^{-1}$, scattering coefficient $\mu_s=150$ cm$^{-1}$, anisotropy factor g=0.8, refractive index of fiber: 1.47, refractive index of medium 1.335 (phantom) or 1.40 (tissue). Again, these optical properties are arbitrary and are simply used as starting parameters for the simulations. Photons which escape to the surface of the medium and are within the numerical aperture (NA) of the fiber (in the present example, the NA is assumed to be 0.12) were stored in an array, containing the exit weight, launch depth (z), net radial distance traveled (r), and number of interactions within the medium prior to escape. Having this information it is possible to scale this escape energy probability map, $E(r_i, z_i)$, to that which would have been obtained from any arbitrary set of optical properties using the scaling relations of Graaff et al., 1993 [17]. It is also possible, using the principle of reciprocity, to determine how much light energy would be absorbed at a given location within the medium were the photon launched at the surface of the tissue using a fiber with a specific numerical aperture. The difference in solid angle between the acceptance of light by the absorber ($4\pi$), and the limited acceptance angle of the fiber (defined by the NA) must be accounted for. Swartling et al. derived the effect of a difference in solid angle between the source and collection, and using this factor, the relationship between $E(r,z)$ and $A(r,z)$ is given by:

$$A(r, z) = \frac{4\pi}{\Delta\Omega} \mu_a^x E(r, z) \quad (1)$$

Where $\Delta\Omega$ is the solid angle corresponding to the fiber's numerical aperture, and $\mu_a^x$ is the absorption coefficient at the excitation wavelength. This relationship allows for the need for only a single set of simulations to be run for generating both the escaping energy and absorption grid, and also enables the elimination of a radial grid, as used by Swartling et al., 2003, which can lead to inaccuracies at short source detector separations [11]. However, as described above, the present subject matter is not limited to using a single set of simulations to determine the absorbed energy density map and the escape energy probability map. In an alternate implementation, separate sets of simulations may be used to determine the absorbed energy density map and the escape energy probability map without departing from the scope of the subject matter described herein.

Not all of this deposited energy is converted to fluorescence, as some is lost due to non-fluorescent absorption. The probability of an absorbed photon generating a fluorescent photon at a given emission wavelength is given by Swartling et al., 2003 [11] as:

$$\phi_{eff}(\lambda^m) = \phi \frac{\mu_a^{xf}}{\mu_a^x} \frac{\eta(\lambda^m)\Delta\lambda}{\int_0^\infty \eta(\lambda)d\lambda} \quad (2)$$

Where $\phi_{eff}$ is the effective quantum yield for a given excitation-emission wavelength pair in the medium of interest, $\phi$ is the fluorescence quantum yield, $\mu_a^{xf}$ is the absorption coefficient of the fluorophore at the excitation wavelength, $\mu_a^x$ is the total absorption coefficient of all absorbers in the medium at the excitation wavelength, m is the emission wavelength, and $\eta(\lambda)$ is the spectral probability distribution of the generated fluorescence as a function of the emission wavelength. This equation thus takes into account the probability that a photon absorbed by the fluorophore will generate fluorescence ($\phi$), the probability an absorbed photon will be absorbed by the fluorophore rather than another absorber ($\mu_a^{xf}/\mu_a^x$), and the probability that a generated fluorescent photon will be emitted at the collected emission wavelength (the remaining terms).

Given the deposited energy grid and Eq. 2, it is then possible to determine the location and intensity of fluorescence generated as a function of emission wavelength at all points within the medium for any given set of optical properties at the excitation wavelength and fluorescence properties ($\phi$, $\mu_a^{xf}$, $\eta(\lambda)$). This is accomplished by taking the product of the absorbed energy and $\phi_{eff}$. Thus the fluorescence generated at each grid element is given by:

$$F_{gen}(r_i, z_j) = \phi_{eff} \times A(r_i, z_j) \quad (3)$$

Where $F_{gen}$ is the fluorescence energy density created within the medium, and A is the absorbed energy density, each as a function of depth and radial distance. The radially dependent fluorescence generated at a given depth is then convolved with the escape probability function to obtain the exit probability of fluorescent photons escaping the surface of the medium to be collected. The quasi discrete Hankel transform, described by Li et al, 1998. was used to perform this convolution [18]. Summing over the entire range of depths within the medium gives the total emitted fluorescence as a function of radial distance. Thus the emitted fluorescence is given by:

$$F_{exit}(r) = \sum_j \Delta z_j \times F_{gen}(r, z_j) * E(r, z_j) \quad (4)$$

Where $F_{exit}(r)$ is the radially dependent fluorescence exiting the surface of the tissue, and $F_{gen}$ is the generated fluorescence at a particular radial distance (r) and depth (z). $E(r,z)$ gives the probability that a photon originating at a depth z will exit the surface a radial distance (r) from its point of origin. $\Delta z$ gives the grid size in the depth dimension for each summed grid element. This gives the fluorescence emitted from the surface of the medium, given a point source illumination. Convolution, following the method of Li et al., 1998 [18], is used to account for the specific probe geometry used. Briefly, this method includes convolving fluorescent photons emitted from point sources at different locations within the turbid medium with the collection surface area of the fiber optic probe. As a result of the model incorporating or accounting for the probe geometry, the model may be used to extract an indication of intrinsic fluorescence from measurements made using any suitable probe geometry.

Note that since $\phi_{eff}$ is a scalar, owing to the associative property of convolution, substituting Eq. 3 into Eq. 4, it can be taken out of the summation in Eq. 4, as:

$$F_{exit}(r) = \phi_{eff} \times \sum_j \Delta z_j \times A(r, z_j) * E(r, z_j) \quad (5)$$

The terms within the summation depend only on the optical properties of the medium at the excitation and emission wavelengths, and not on the fluorescence properties of the medium. In particular, A is a function of the optical properties at the excitation wavelength, and E is a function of the optical properties at the emission wavelength. Furthermore, note that in Eq. 2, for a known fluorophore, the wavelength dependent extinction coefficients and emission spectra are known. $\phi_{eff}$ can thus be expressed as the product of the fluorophore concentration, the quantum yield, and a set of wavelength dependent constants, as shown below:

$$\phi_{eff}(\lambda^m) = \phi \frac{\mu_a^{xf}}{\mu_a^x} \frac{\eta(\lambda^m)\Delta\lambda}{\int_0^\infty \eta(\lambda)d\lambda} = \phi C \times \frac{2.303\varepsilon^{xf}}{\mu_a^x} \frac{\eta(\lambda^m)\Delta\lambda}{\int_0^\infty \eta(\lambda)d\lambda} \quad (6)$$

Where C is the fluorophore concentration and $\varepsilon^{xf}$ is the extinction coefficient of the fluorophore at the excitation wavelength. Thus, for a known fluorophore it is possible to determine the product of the quantum yield and concentration of the fluorophore from the fluorescence spectra using this approach. Incorporating the specific probe geometry used, and combining Equations 5 and 6, we get:

$$F_{meas}(\lambda^m) = \phi C \times S \times \frac{2.303\varepsilon^{xf}}{\mu_a^x} \frac{\eta(\lambda^m)\Delta\lambda}{\int_0^\infty \eta(\lambda)d\lambda} \times P(r) \times \sum_j \Delta z_j \times A(r, z_j) * E(r, z_j) \quad (7)$$

or $$\phi C = \frac{F_{meas}(\lambda^m)}{\frac{2.303\varepsilon^{xf}}{\mu_a^x} \frac{\eta(\lambda^m)\Delta\lambda}{\int_0^\infty \eta(\lambda)d\lambda} \times P(r) \times \sum_j \Delta z_j \times A(r, z_j) * E(r, z_j)} \times \frac{1}{S} \quad (8)$$

Where $F_{meas}$ is the fluorescence measured using a particular probe geometry, given the optical and fluorescence properties ($\phi$, $\varepsilon^{xf}$, $\eta(\lambda)$, C) of the medium, and P(r) gives the probability that a photon which exits the surface of the medium a distance r from the point of origin, will be collected by the collection fiber for the probe geometry used (this is obtained using convolution as per Palmer and Ramanujam, 2006 [15]). S is a scaling factor necessary to account for the difference in magnitude between the Monte Carlo simulations (which are on an absolute scale) and the measured result (which is typically relative to a fluorescence standard). This factor must be determined using a phantom measurement in order to pool data collected using different instruments or probe geometries. For a single instrument setup, it can be set to unity to leave the data on a relative scale.

Phantom Validation

The model described above was tested using synthetic tissue phantoms. Phantoms were made using Hemoglobin (Catalogue No. H0267, Sigma-Aldrich Corp., St. Louis, Mo., United States of America) as the absorber, furan-2 (Exiton, Inc. Dayton, Ohio) as the fluorophore, and polystyrene spheres (Catalogue No. 07310, Polysciences, Inc., Warrington, Pa., United States of America) as the scatterer. Three sets of phantoms were prepared, having low, medium, and high scattering properties. Into each phantom, 0.6 µg/ml of furan-2 was added, and varying concentrations of hemoglobin were added in to change the absorption properties of the medium, yielding a total of 11 phantoms. The absorption coefficient was determined using a spectrophotometer (Cary 300, Varian, Inc., Palo Alto, Calif., United States of America)), and the scattering coefficient was calculated using Mie theory [19], taking into account the wavelength dependent refractive index of polystyrene spheres [20] and water [21]. Table 1 summarizes the optical properties of the phantoms used over the wavelength range of 300-800 nm. Phantoms 1-4 correspond to low scattering, 5-8 correspond to medium scattering, and 9-11 correspond to high scattering. Within each scattering level, as the phantom number increases, more hemoglobin has been added, so the absorption coefficients increase, while the scatterer is diluted slightly, so the scattering coefficients decrease. The SPEX® SkinSkan fluorometer (HORIBA Jobin Yvon Inc., Edison, N.J., United States of America) and probe [15, 16], were used for making all experimental measurements.

TABLE 1

Summary of the Optical Properties of the Phantoms used to Validate the Fluorescence Model over the Wavelength Range of 300-800 nm

| Phantom Number | Absorption coefficient, $\mu_a$ (cm$^{-1}$) | | | Reduced Scattering Coefficient, $\mu_s'$ (cm$^{-1}$) | | |
|---|---|---|---|---|---|---|
| | Min | Max | Mean | Min | Max | Mean |
| 1 | 0.0 | 0.9 | 0.1 | 3.3 | 6.7 | 4.3 |
| 2 | 0.0 | 6.8 | 0.8 | 3.2 | 6.5 | 4.2 |
| 3 | 0.0 | 12.4 | 1.5 | 3.1 | 6.4 | 4.1 |
| 4 | 0.0 | 22.9 | 2.8 | 3.0 | 6.1 | 3.9 |
| 5 | 0.0 | 0.9 | 0.1 | 9.8 | 20.0 | 12.9 |
| 6 | 0.0 | 6.8 | 0.8 | 9.5 | 19.5 | 12.6 |
| 7 | 0.0 | 12.4 | 1.5 | 9.3 | 19.0 | 12.3 |
| 8 | 0.0 | 22.9 | 2.8 | 8.8 | 18.2 | 11.7 |
| 9 | 0.0 | 6.7 | 0.8 | 15.8 | 32.4 | 20.9 |
| 10 | 0.0 | 12.3 | 1.5 | 15.4 | 31.6 | 20.4 |
| 11 | 0.0 | 22.7 | 2.8 | 14.7 | 30.2 | 19.5 |

Note:
Phantoms 1-4 correspond to low scattering, 5-8 correspond to medium scattering and 9-11 correspond to high scattering.

The diffuse reflectance (300-800 nm) and fluorescence (330 nm excitation) were measured from each sample by placing the probe just in contact with the surface of the phantom. Then the diffuse reflectance was used to extract the optical properties of each sample using a Monte Carlo model of diffuse reflectance using procedures described in Palmer and Ramanujam, 2006 [15]. In addition, the known optical properties (taken from Mie theory, and the spectrophotometer measurement) were used as inputs to the fluorescence model. This allows for an assessment of the propagation of errors from the reflectance model to the fluorescence model. In order to illustrate the effectiveness of the model in determining the prevalence of the fluorophore within the medium, Equation 8 was solved for the product:

$$\phi \times \frac{\eta(\lambda^m)\Delta\lambda}{\int_0^\infty \eta(\lambda)d\lambda} \qquad (9)$$

The concentration was divided out to account for the fact that as absorber was added, the fluorophore concentration was diluted slightly. Assuming that the quantum yield, $\phi$, is constant in each of the phantoms, this quantity plotted as a function of wavelength should indicate the ability of this method to both extract the concentration, and retrieve the intrinsic fluorescence line shape. The ideal result would yield overlapping curves for each of the phantoms, with identical intensities and line shapes. The degree to which these quantities deviate from each other indicates the errors that would be obtained in calculating the fluorophore concentrations. The quantum yield was not determined for this fluorophore, but using a quantum yield of 1, S was calculated to be 569±16, averaged across all phantoms. Note that as applied to tissue, Equation 8 would be solved for the product:

$$\phi C \varepsilon^f \times \frac{\eta(\lambda^m)\Delta\lambda}{\int_0^\infty \eta(\lambda)d\lambda} \qquad (10)$$

since the concentration quantum yield, and fluorophore extinction coefficients are unknowns. It is possible that the quantum yields and extinction coefficients, and emission efficiencies could be independently determined, allowing an absolute determination of fluorophore concentration in tissue, but that is beyond the scope of this manuscript. Thus this model would report a quantity that is proportional to the product of these parameters, which is referred to as the intrinsic fluorescence.

Results

Figure 3A:
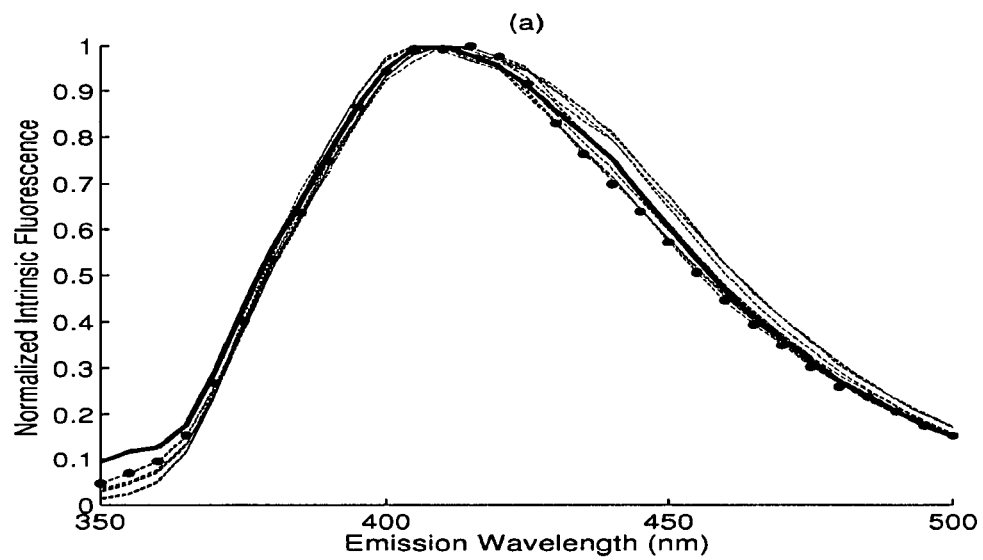
FIGS. 3A-3D are plots of extracted intrinsic fluorescence spectra, acquired at 330 nm excitation. In particular.
Figure 3B:
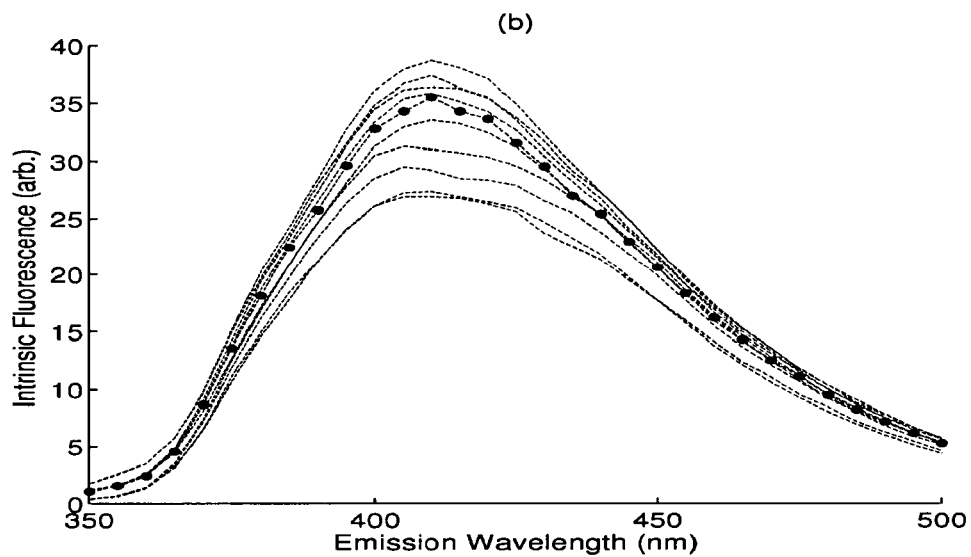
Figure 3C:
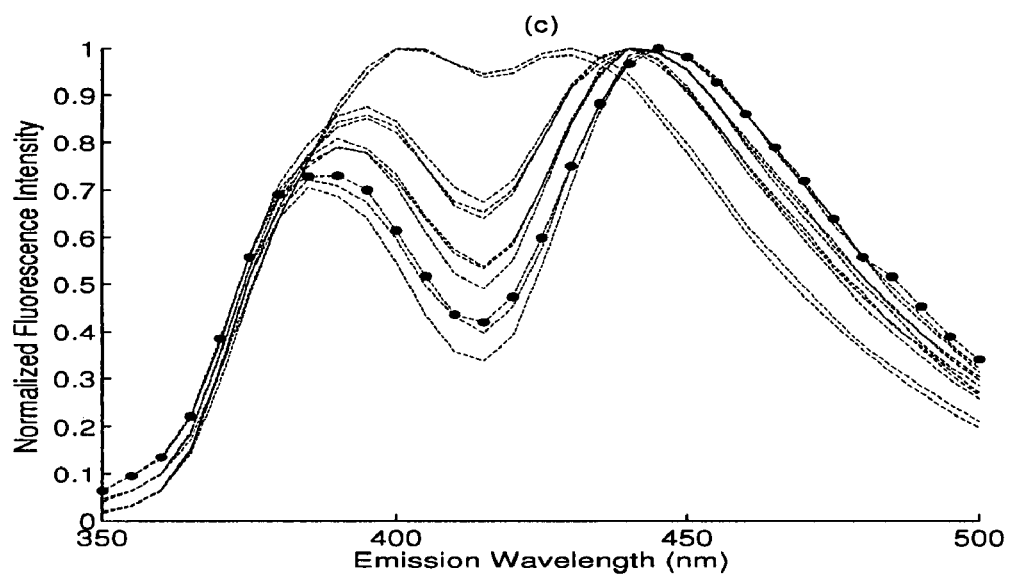
Figure 3D:
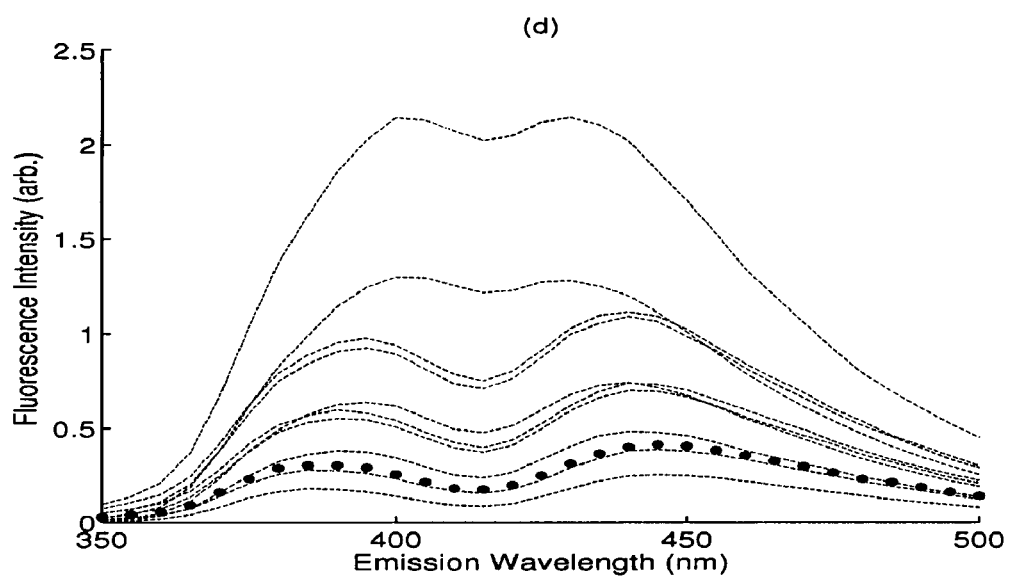

FIGS. 3A and 3B show the product in Eq. (9) for both normalized (FIG. 3A) and non-normalized (FIG. 3B) fluorescence spectra. The fluorescence line shape in the absence of any absorber or scatterer is also shown (bold black line in FIG. 3A) and can be seen to be very similar to the extracted line shape. The optical properties used in the fluorescence model were extracted from each sample using the diffuse reflectance model (Palmer and Ramanujam, 2006, 2006) [15, 16]. FIGS. 3C and 3D show the corresponding raw fluorescence spectra measured from the phantoms. All spectra were acquired at 330 nm excitation. In all plots in FIGS. 3A-3D, the phantom with the highest absorption and scattering properties (phantom 11) is shown using the circle markers to illustrate the ability of the model to correct for absorption and scattering in this extreme case.

It can be seen that the model corrects for the original large differences in magnitude and line shape present due to the differences in absorption and scattering in each of the phantoms. The concentration could be solved for in Equation 8, by assuming the quantum yield was fixed for all phantoms, and setting the scaling factor, S, to be equal to the mean value obtained from each of the phantoms, determined to be 569±16. The RMS error in extracting the concentration of furan in these phantoms using Equation 8 at the peak emission wavelength is ±12%.

Discussion

The subject matter described herein a methodology by which the intrinsic fluorescence spectra can be extracted from combined fluorescence and diffuse reflectance spectral data, which are commonly measured in a variety of clinical and preclinical studies. This allows for more biologically relevant interpretation of these data, since they can be more directly related to underlying tissue properties (fluorophore concentrations or microenvironment). The application of this model to phantoms was relatively straightforward, since all of the constituents were known and well characterized, and reasonably good results were obtained in extracting the intrinsic fluorescence line shape and fluorophore concentration. The significant advantages of this model include 1) it does not require any assumptions regarding the underlying fluorescence properties in order to calculate the intrinsic fluorescence spectra, 2) it is able to account for any arbitrary probe geometry, 3) it does not require extensive empirical calibration, and can easily be adapted to any probe geometry, and 4) it is accurate for cases of high absorption and small source-detector separation.

The subject matter described herein can be used to extract intrinsic fluorescence from biological tissues. The application of the subject matter described herein to tissue can be challenging due to the presence of multiple absorbers, scatterers, and fluorophores of uncertain properties. However, the reflectance model referenced herein has been applied to tissue data, and the addition of the fluorescence model is relatively straightforward since it does not require any assumptions regarding the properties of the fluorophores in order to retrieve the intrinsic fluorescence. It may be desirable to obtain the actual concentration of the fluorophore, however this does require some additional knowledge of the fluorophore properties that steady state fluorescence measurements cannot provide, including the quantum yield, and fluorophore extinction coefficient.

In conclusion, the subject matter described herein includes a methodology by which the intrinsic fluorescence spectra can be extracted from tissue fluorescence spectra. This approach is flexible in is application to any arbitrary probe geometry, and is also valid in the UV-VIS, where absorption is high relative to scattering. Furthermore, though it was applied in this case to endogenous sources of fluorescence, it could also be used to characterize the prevalence of exogenous sources of fluorescence.

REFERENCES

The disclosures of all of the references listed herein are hereby incorporated herein by reference in their entireties.

[1] N. Ramanujam, "Fluorescence Spectroscopy In Vivo," in *Encyclopedia of Analytical Chemistry*, R. Meyers, Ed.: John Wiley and Sons, Ltd., 2000, pp. 20-56.

[2] N. C. Biswal, S. Gupta, N. Ghosh, and A. Pradhan, "Recovery of turbidity free fluorescence from measured fluorescence: an experimental approach," *Optics Express*, vol. 11, 2003.

[3] S. K. Chang, N. Marin, M. Follen, and R. Richards-Kortum, "Model-based analysis of clinical fluorescence spectroscopy for in vivo detection of cervical intraepithelial dysplasia," *Journal of Biomedical Optics*, vol. 11, pp. 024008, 2006.

[4] K. R. Diamond, T. J. Farrell, and M. S. Patterson, "Measurement of fluorophore concentrations and fluorescence quantum yield in tissue-simulating phantoms using three diffusion models of steady-state spatially resolved fluorescence," *Physics in Medicine and Biology*, vol. 48, pp. 4135-49, 2003.

[5] K. R. Diamond, M. S. Patterson, and T. J. Farrell, "Quantification of fluorophore concentration in tissue-simulating media by fluorescence measurements with a single optical fiber," *Applied Optics*, vol. 42, pp. 2436-42, 2003.

[6] A. J. Durkin, S. Jaikumar, N. Ramanujam, and R. Richards-Kortum, "Relation between fluorescence spectra of dilute and turbid samples," *Applied Optics*, vol. 33, pp. 414-23, 1994.

[7] C. M. Gardner, S. L. Jacques, and A. J. Welch, "Fluorescence spectroscopy of tissue: recovery of intrinsic fluorescence from measured fluorescence," *Applied Optics*, vol. 35, pp. 1780-92, 1996.

[8] M. G. Muller, I. Georgakoudi, Z. Qingguo, W. Jun, and M. S. Feld, "Intrinsic fluorescence spectroscopy in turbid media: disentangling effects of scattering and absorption," *Appl Opt*, vol. 40, pp. 4633-46, 2001.

[9] Q. Zhang, M. G. Muller, J. Wu, and M. S. Feld, "Turbidity-free fluorescence spectroscopy of biological tissue," *Optics Letters*, vol. 25, pp. 1451-1453, 2000.

[10] M. Sinaasappel and H. J. C. M. Sterenborg, "Quantification of the hematoporphyrin derivative by fluorescence measurement using dual-wavelength excitation and dual-wavelength detection," *Applied Optics, vol.* 32, pp. 541-8, 1993.

[11] J. Swartling, A. Pifferi, A. M. Enejder, and S. Andersson-Engels, "Accelerated Monte Carlo models to simulate fluorescence spectra from layered tissues," *J Opt Soc Am A Opt Image Sci Vis*, vol. 20, pp. 714-27, 2003.

[12] R. Weersink, M. S. Patterson, K. Diamond, S. Silver, and N. Padgett, "Noninvasive measurement of fluorophore concentration in turbid media with a simple fluorescence/reflectance ratio technique," *Applied Optics*, vol. 40, pp. 6389-95, 2001.

[13] J. Wu, M. S. Feld, and R. P. Rava, "Analytical model for extracting intrinsic fluorescence in turbid media," *Applied Optics*, vol. 32, pp. 3585-95, 1993.

[14] N. N. Zhadin and R. R. Alfano, "Correction of the internal absorption effect in fluorescence emission and excitation spectra from absorbing and highly scattering media: theory and experiment," *Journal of Biomedical Optics*, vol. 3, pp. 171-86, 1998.

[15] G. M. Palmer and N. Ramanujam, "Monte Carlo-based inverse model for calculating tissue optical properties. Part I: Theory and validation on synthetic phantoms," *Appl Opt*, vol. 45, pp. 1062-71, 2006.

[16] G. M. Palmer, C. Zhu, T. M. Breslin, F. Xu, K. W. Gilchrist, and N. Ramanujam, "Monte Carlo-based inverse model for calculating tissue optical properties. Part II: Application to breast cancer diagnosis," *Appl Opt*, vol. 45, pp. 1072-8, 2006.

[17] R. Graaff, M. H. Koelink, F. F. M. de Mul, W. G. Zijlstra, A. C. M. Dassel, and J. G. Aarnoudse, "Condensed Monte Carlo simulations for the description of light transport [biological tissue]," *Appl Opt, vol.* 32, pp. 426-34, 1993.

[18] Y. Li, H. Meichun, C. Mouzhi, C. Wenzhong, H. Wenda, and Z. Zhizhong, "Quasi-discrete Hankel transform," *Opt Lett*, vol. 23, pp. 409-11, 1998.

[19] S. Prahl, "Mie Scattering Program", 2003. Available: http://omlc.ogi.edu/software/mie.

[20] X. Ma, J. Q. Lu, R. S. Brock, K. M. Jacobs, P. Yang, and X. H. Hu, "Determination of complex refractive index of polystyrene microspheres from 370 to 1610 nm," *Phys Med Biol*, vol. 48, pp. 4165-72, 2003.

[21] International Association for the Properties of Water and Steam, "Release on the Refractive Index of Ordinary Water Substance as a Function of Wavelength, Temperature, and Pressure", 1997. Available: http://www.iapws.org/relguide/rindex.pdf.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for modeling fluorescence of a turbid medium and for using the model to determine intrinsic fluorescence in the turbid medium, the method comprising:

illuminating a turbid medium of interest with an electromagnetic radiation source using a probe of a particular geometry that comprises one or more collection fibers and one or more illumination fibers and detecting measured fluorescence for the turbid medium using the probe;

running at least one set of Monte Carlo simulations to determine an escape energy probability map and an absorbed energy density map for the turbid medium; and determining, in a manner that accounts for the geometry of the probe using a function that considers the surface areas of the one or more collection fibers and the one or more illumination fibers of the probe and photons escaping the turbid medium, and using the measured fluorescence, the absorbed energy density map, and the escape energy probability map, an indication of intrinsic fluorescence of the turbid medium.

2. The method of claim 1 wherein running at least one set of Monte Carlo simulations includes:

running a single set of Monte Carlo simulations where photons are launched from varying depths in a turbid medium with an arbitrary set of optical properties to determine an escape energy probability map for the medium with the arbitrary set of optical properties;

scaling the escape energy probability map for the medium with the arbitrary set of optical properties using optical properties for the medium of interest to determine the escape energy probability map for the medium of interest; and using a reciprocity principle to determine the absorbed energy density map for the medium of interest.

3. The method of claim 1 wherein running at least one set of Monte Carlo simulations includes:

running a first set of Monte Carlo simulations where photons are launched from outside of a turbid medium with an arbitrary set of optical properties to determine an absorbed energy density map for the medium with the arbitrary set of optical properties and scaling the absorbed energy density map for the turbid medium with the arbitrary set of optical properties using optical properties for the medium of interest to determine the absorbed energy density map for the medium of interest; and running a second set of Monte Carlo simulations where photons are launched from varying depths in the turbid medium with the arbitrary set of optical properties to determine an escape energy probability map for the medium with the arbitrary set of optical properties and scaling the escape energy probability map for the medium with the arbitrary set of optical properties using optical properties for the medium of interest to determine the escape energy probability map for the medium of interest.

4. The method of claim 1 wherein determining the intrinsic fluorescence of the medium includes determining a product of a quantum yield and the concentration of at least one known fluorophore.

5. The method of claim 1 wherein determining the intrinsic fluorescence of the medium in the medium includes determining the concentration of at least one known fluorophore in the medium.

6. The method of claim 1 wherein determining an indication of the intrinsic fluorescence of the medium includes determining the indication of the intrinsic fluorescence as a function of a scaling factor that accounts for a difference in magnitude between the at least one Monte Carlo simulation and the measured fluorescence.

7. The method of claim 1 wherein determining an indication of the intrinsic fluorescence of the medium accounting for the geometry of the probe includes determining the indication of the intrinsic fluorescence in a manner such that the indication will be the same for the turbid medium when fluorescence is measured with different probe geometries.

8. The method of claim 1 wherein determining an indication of the intrinsic fluorescence accounting for geometry of the probe includes determining a probability that a photon exiting the medium of interest will be detected by the probe given the geometry of the probe.

9. The method of claim 8 wherein determining the probability includes convolving photons generated by a point source during the at least one simulation with illumination and collection areas of the probe.

10. The method of claim 1 wherein the turbid medium of interest comprises a biological tissue sample.

11. A system for modeling fluorescence of a turbid medium and for using the model to determine intrinsic fluorescence in the turbid medium, the system comprising:
a probe for illuminating a turbid medium of interest with electromagnetic radiation generated by an electromagnetic radiation source, the probe having a particular geometry that comprises one or more collection fibers and one or more illumination fibers and the probe detecting measured fluorescence for the turbid medium; and
a processor for running at least one set of Monte Carlo simulations to determine an escape energy probability map and an absorbed energy density map for the turbid medium, for determining, using the measured fluorescence, the absorbed energy density map, and the escape energy probability map, wavelength-dependent extinction coefficients and emission spectra for a known fluorophore, and accounting for the geometry of the probe using a function that considers the surface areas of the one or more collection fibers and the one or more illumination fibers of the probe and photons escaping the turbid medium, an indication of intrinsic fluorescence of the turbid medium.

12. The system of claim 11 wherein the processor is adapted to, in running at least one set of Monte Carlo simulations:
run a single set of Monte Carlo simulations where photons are launched from varying depths in a turbid medium with an arbitrary set of optical properties to determine an escape energy probability map for the medium with the arbitrary set of optical properties;
scale the escape energy probability map for the medium with the arbitrary set of optical properties using optical properties for the medium of interest to determine the escape energy probability map for the medium of interest; and
use a reciprocity principle to determine the absorbed energy density map for the medium of interest.

13. The system of claim 11 wherein, in running at least one set of Monte Carlo simulations, the processor is adapted to:
run a first set of Monte Carlo simulations where photons are launched from outside of a turbid medium with an arbitrary set of optical properties to determine an absorbed energy density map for the medium with the arbitrary set of optical properties and scale the absorbed energy density map for the turbid medium with the arbitrary set of optical properties using optical properties for the medium of interest to determine the absorbed energy density map for the medium of interest; and
run a second set of Monte Carlo simulations where photons are launched from varying depths in the turbid medium with the arbitrary set of optical properties to determine an escape energy probability map for the medium with the arbitrary set of optical properties and scale the escape energy probability map for the medium with the arbitrary set of optical properties using optical properties for the medium of interest to determine the escape energy probability map for the medium of interest.

14. The system of claim 11 wherein, in determining the intrinsic fluorescence of the medium, the processor is adapted to determine a product of a quantum yield and the concentration of at least one known fluorophore.

15. The system of claim 11 wherein, in determining the intrinsic fluorescence of the medium, the processor is adapted to determine the concentration of at least one known fluorophore in the medium.

16. The system of claim 11 wherein the processor is adapted to determine the intrinsic fluorescence as a function of a scaling factor that accounts for a difference in magnitude between the at least one Monte Carlo simulation and the measured fluorescence.

17. The system of claim 11 wherein the processor is adapted to determine the indication of the intrinsic fluorescence in a manner such that the indication of the intrinsic fluorescence will be the same for the turbid medium when fluorescence is measured with different probe geometries.

18. The system of claim 11 wherein the processor is adapted to determine a probability that a photon exiting the medium of interest will be detected by the probe given the geometry of the probe.

19. The system of claim 18 wherein, in determining the probability, the processor is adapted to convolve photons generated by a point source during at least one simulation with the illumination and collection areas of the probe.

20. The system of claim 11 wherein the turbid medium of interest comprises a biological tissue sample.

* * * * *

UNITED STATES PATENT AND TRADEMARK OFFICE
CERTIFICATE OF CORRECTION

PATENT NO.        : 7,818,154 B2                                   Page 1 of 1
APPLICATION NO.   : 11/725141
DATED             : October 19, 2010
INVENTOR(S)       : Palmer et al.

It is certified that error appears in the above-identified patent and that said Letters Patent is hereby corrected as shown below:

Title page, OTHER PUBLICATIONS, LINE 1
  replace "odel"
  with --Model--

Signed and Sealed this

Twenty-first Day of December, 2010

David J. Kappos
*Director of the United States Patent and Trademark Office*